United States Patent
Reimer et al.

(10) Patent No.: US 9,510,754 B2
(45) Date of Patent: Dec. 6, 2016

(54) ILLUMINATION ARRANGEMENT AND SURGICAL MICROSCOPE INCORPORATING THE SAME

(71) Applicant: Carl Zeiss Meditec AG, Jena (DE)

(72) Inventors: Peter Reimer, Ellwangen (DE); Juergen Liegel, Oberkochen (DE); Markus Bausewein, Otterfing (DE)

(73) Assignee: Carl Zeiss Meditec AG, Jena (DE)

( * ) Notice: Subject to any disclaimer, the term of this patent is extended or adjusted under 35 U.S.C. 154(b) by 7 days.

(21) Appl. No.: 14/747,829

(22) Filed: Jun. 23, 2015

(65) Prior Publication Data

US 2015/0374234 A1 Dec. 31, 2015

(30) Foreign Application Priority Data

Jun. 26, 2014 (DE) .................. 10 2014 212 372

(51) Int. Cl.
| | | |
|---|---|---|
| *A61B 3/10* | (2006.01) | |
| *A61B 3/14* | (2006.01) | |
| *G02B 21/08* | (2006.01) | |
| *G02B 21/12* | (2006.01) | |
| *A61B 3/13* | (2006.01) | |
| *G02B 19/00* | (2006.01) | |

(52) U.S. Cl.
CPC . *A61B 3/14* (2013.01); *A61B 3/13* (2013.01); *G02B 19/0066* (2013.01); *G02B 21/082* (2013.01); *G02B 21/12* (2013.01)

(58) Field of Classification Search
CPC ............. A61B 3/14; A61B 3/12; A61B 3/102; A61B 3/135; A61B 3/0058; A61B 3/1173; A61B 3/10
USPC 351/221, 207, 220, 246, 206, 205; 359/389, 385
See application file for complete search history.

(56) References Cited

U.S. PATENT DOCUMENTS

| | | | |
|---|---|---|---|
| 4,852,985 A | 8/1989 | Fujihara et al. | |
| 5,760,952 A * | 6/1998 | Koetke | A61B 3/132 351/205 |
| 5,914,771 A * | 6/1999 | Biber | A61B 3/156 351/221 |

(Continued)

FOREIGN PATENT DOCUMENTS

EP 1 997 423 A1 12/2008

OTHER PUBLICATIONS

English translation and the Office action of the German Patent Office dated Mar. 27, 2015 in German patent application 10 2014 212 372.0 on which the claim of priority is based.

(Continued)

*Primary Examiner* — Hung Dang
(74) *Attorney, Agent, or Firm* — Walter Ottesen, P.A.

(57) ABSTRACT

An illumination arrangement includes illumination optics defining an optical axis and a light source for generating at least one illumination beam path for illuminating an object field at a specific illumination angle with a viewing beam path. At least one mirror is provided in the illumination beam path for deflecting light from the light source and the mirror has a longitudinal extent along the optical axis. A light-emitting surface region of the light source is variable (x) perpendicular to the optical axis without movable components. The illumination optics are embodied in such a way for obtaining a desired illumination that an illumination pupil is imaged within the longitudinal extent of the mirror.

12 Claims, 6 Drawing Sheets

(56) References Cited

U.S. PATENT DOCUMENTS

| | | |
|---|---|---|
| 7,307,785 B2 | 12/2007 | Obrebski et al. |
| 7,561,329 B2 | 7/2009 | Zahniser et al. |
| 7,697,199 B2 | 4/2010 | Reimer et al. |
| 8,177,364 B2 | 5/2012 | Reimer et al. |
| 8,708,493 B2 | 4/2014 | Reimer et al. |
| 2003/0042493 A1 | 3/2003 | Kazakevich |
| 2007/0211460 A1 | 9/2007 | Ravkin |
| 2007/0247691 A1 | 10/2007 | Obrebski et al. |
| 2009/0122398 A1* | 5/2009 | Machida ............ G02B 21/0012 359/388 |
| 2012/0057013 A1 | 3/2012 | Ishiwata |
| 2015/0253557 A1 | 9/2015 | Kalkbrenner |

OTHER PUBLICATIONS

English translation and the extended Search Report of the European Patent Office dated Nov. 19, 2015 in the corresponding European patent application 15172223.8-1562.

* cited by examiner

ILLUMINATION ARRANGEMENT AND SURGICAL MICROSCOPE INCORPORATING THE SAME

CROSS REFERENCE TO RELATED APPLICATION

This application claims priority of German patent application No. 10 2014 212 372.0, filed Jun. 26, 2014, the entire content of which is incorporated herein by reference.

FIELD OF THE INVENTION

The invention relates to an illumination arrangement, in particular of a surgical microscope.

BACKGROUND OF THE INVENTION

EP 1 997 423 B1 has disclosed a surgical microscope with an illumination arrangement, comprising illumination optics and a light source. Here, a near-axis or coaxial illumination can be obtained with a first illumination beam path and an off-axis illumination can be obtained with a second illumination beam path. Here, an angle of, for example, 2° or 6° is selected between an observation beam path and illumination beam path. Using such a surgical microscope it is possible, inter alia, to carry out cataract surgery. Furthermore, these surgical microscopes, or the illumination arrangements thereof, are embodied in such a way that it is possible in the eye to be examined to generate the red reflex, that is, the lighting up red of the eye pupil in the case of near-axis illumination, which is known per se. Therefore, structures which are transparent per se, for example, of an eye lens to be removed, can be shown. This is realized using either coaxial illumination or a lateral illumination with a simpler setup, for example under an angle of incidence of 2°. As an alternative to a 2° illumination, or in addition thereto, it is also possible that a larger illumination angle, for example, 6°, is demanded so as to obtain even higher contrasting, that is, light/shadow distribution, and, in particular, to spare the macula on the retina if no red reflex is required, as in the case of a corneal transplant.

Furthermore, United States patent application publication 2007/0247691 describes an illumination arrangement for a surgical microscope which, for example, is used in ophthalmic surgery. The illumination arrangement comprises a mirror for deflecting light, wherein the mirror extends over a length region along an optical axis of the illumination arrangement. This means that the plane of the mirror is inclined in relation to the optical axis and the projection of the mirror plane onto the optical axis, as seen in the cross section, has a certain longitudinal extent. The illumination arrangement comprises a light source, which can be made of a matrix, in particular made of organic light-emitting diodes (OLEDs). Depending on which of these very small light sources is activated, it is possible, as seen in a plane perpendicular to an optical axis of the illumination arrangement, to obtain desired illumination geometries, that is, for example, a 2° or 6° illumination. In particular, no mechanical components are required for generating different illumination geometries. However, uniform illumination of an object field or the targeted illumination of a specific portion thereof, that is, for example, of an eye to be operated, is not always ensured in this case.

SUMMARY OF THE INVENTION

It is an object of the invention to provide a surgical microscope, or the illumination arrangement therefor, wherein the illumination desired by the user, in particular different illumination angles, is realized in a simple manner and a homogeneous illumination is obtained.

The illumination arrangement of the invention is for an optical instrument defining a viewing beam path. The illumination arrangement includes: an illumination optic defining an optical axis; a light source for generating an illumination beam path for illuminating an object field at a specific illumination angle with the viewing beam path; a mirror arranged in the illumination beam path and being configured to deflect the light of the light source; the mirror having a longitudinal extent along the optical axis; the light source having a light-emitting surface region variable perpendicularly to the optical axis without movable parts; and, the illumination optic being configured to image an illumination pupil within the longitudinal extent of the mirror.

In a manner known per se, a light-emitting surface area of the light source is variable perpendicular to the optical axis of the illumination optics without movable components. Here, the light source should be understood to mean that unit of the illumination arrangement from which light is introduced into the actual surgical microscope via illumination optics. Therefore, it is possible to modify an angle, at which an illumination beam path, which emanates from this surface area and, for example, is incident on a patient's eye, relative to the observation beam path in the case of a suitable selection of the illumination optics. It is clear in this case that this surface area of the light source can be variable not only in, for example, a first x-direction perpendicular to the optical axis of the illumination optics but also, additionally or alternatively, in a y-direction, perpendicular to the first x-direction, in a plane perpendicular to the optical axis of the illumination optics. By way of example, as described in more detail below, a plurality of light-emitting areas, which are to be controlled separately, in a light source can be arranged relatively close to one another such that, depending on the number, intensity and position of the activated light-emitting areas, an area centroid of the specific light emission from the light source changes, at least in a direction perpendicular to the optical axis of the illumination optics. Here, the specific light emission is the light power per unit area of the light source, which is emitted into the whole solid angle. In particular, it is therefore possible to dispense with movable components such as, for example, mechanical stops. What is likewise made possible is that, depending on the selection of the light-emitting surface area, practically only precisely the illumination beam path that is desired is generable. Consequently, it is possible to avoid superfluous light generation which, for example, could lead to an unwanted heat influx.

Furthermore, the illumination arrangement is embodied in such a way that the illumination optics image an illumination pupil within the longitudinal extent of the mirror. Consequently, depending on the location at which the illumination pupil is imaged within the longitudinal extent, it is possible to obtain a desired illumination angle, in particular on a patient's eye, for example a +/−2° illumination in order to obtain a homogeneous red reflex. It is likewise possible to obtain a 6° illumination if no red reflex is required.

Preferably, such an illumination arrangement is used at an ophthalmic surgical microscope. However, it can also be used in laboratory microscopes, technoscopes, stereo microscopes or any other surgical microscopes from other disciplines. It is also clear to a person skilled in the art that a surgical microscope, at which such an illumination arrangement is arranged, may comprise one, two or more observation beam paths, in particular also stereoscopic observation beam paths. By way of example, provision is made for a main microscope for the surgeon and an assistant's microscope.

The basic setup of a surgical microscope with an associated illumination arrangement can be gathered, inter alia, from EP 1 997 423 B1 or U.S. Pat. Nos. 8,177,364 or 8,708,493, the disclosures of which in this respect are explicitly referred to.

In a preferred embodiment, it is no longer only a single light source such as, for example, a halogen lamp or two spatially separated light sources for different illumination angles that are used as a light source, but rather it is only a single light source which has a plurality of light-emitting areas which then respectively form the aforementioned surface areas. Here, the light source is configured in such a way that this plurality of areas are activatable independently of one another. This means that, for example, one, two, three or four areas can emit light together or independently of one another. It is also preferable for the power of the light-emitting areas to be actuatable independently from one another in order to obtain different illumination angles. Preferably, each one of the individual light-emitting areas is independently subjectable to closed-loop and/or open-loop control. That is, they can be switched on and off or dimmed individually, in groups or all together. In principle, the light source can also have more light-emitting areas. Particularly in the case of an embodiment, described below, as a multichip emitter LED, it is possible, due to the arrangement of the luminous areas or of the individual segments of the LED, to realize an illumination as desired, that is, for example, a 2° illumination or a 6° illumination. This emerges from the fact that the embodiment of illumination optics can be selected in such a way that, depending on the activation of one or more areas, for example, a 2° or 6° illumination is realizable, depending on the arrangement of the light source or the light-emitting areas thereof. By way of example, a different angle of the illumination beam path is obtained if one or two light-emitting areas above the optical axis of the illumination optics are activated than if two light-emitting areas below the optical axis are activated. A corresponding embodiment of the illumination optics is implemented on the basis of the dimensioning and type of light source and the dimensions and properties of, for example, the surgical microscope. In order to realize a light source with a plurality of light-emitting areas, use can be made of, for example, LEDs, lasers, converters excited by lasers, optical waveguides, DMDs (digital micromirror devices) and the like. It is also conceivable that, for example, a plurality of individual LEDs or other light-emitting areas/objects are arranged close to one another and form a single light source. However, this leads to larger installation size, in particular of the illumination optics of the illumination arrangement.

In a preferred manner, the light source of the illumination arrangement is a multichip emitter LED, as is currently available under the trade names Cree MCE or SEOUL P4. These LEDs have four light-emitting areas or segments, which are actuatable or activatable independently of one another in order, depending on the activated light-emitting area, to obtain a different illumination angle. By way of example, such an LED has four chips, which form the four light-emitting areas with an edge length of in each case approximately 1 to 4 mm.

Preferably, selective activation or actuation of the light-emitting areas of the light source can be used to realize a 2° or 6° illumination, known per se, with the aforementioned illumination angles in order, for example, to be able to illuminate an eye of a patient to be examined in a desired manner. To this end, the illumination optics can be configured accordingly in order to obtain a desired illumination angle depending on the angle of incidence of one of the light-emitting areas.

What is furthermore proposed is that the various light-emitting areas of the light source are respectively able to have different colors and/or brightness levels. By way of example, one light-emitting area can have a higher red component in order, in particular, to generate the desired red reflex in the eye of a patient. In contrast, a different light-emitting area can have a higher blue component in the emitted spectrum in order to generate a cold-white ambient illumination of the eye. By way of example, an exposure of the macula can be reduced by the modifiable brightness levels.

What is proposed in respect of the embodiment of the illumination arrangement is that at least one, preferably two or more, in particular three, mirrors are provided, wherein one or more mirrors are illuminated depending on the number and arrangement of the activated light-emitting areas or the light-emitting surface areas of the light source. Two mirrors are advantageous, particularly in the case of systems with an assistant's microscope. In principle, use can also be made of split and/or bored-through and/or partly coated mirrors and/or beam splitters. In this embodiment, the illumination pupil is imaged on the optical axis within the longitudinal extent of the projections of the mirrors. Here, the illumination pupil need not necessarily be imaged directly on one mirror itself but can also be imaged between two mirrors, as seen along the optical axis.

What is furthermore proposed is that the light source itself is displaceable along the optical axis in order to project the light emanating therefrom, or the illumination pupil, through the illumination optics to a desired location along the optical axis.

Finally, what is proposed is that the light source has at least three light-emitting areas, which are arranged distributed perpendicular to the optical axis, in particular offset to one another in two directions. Consequently, it is possible to assign, for example, precisely one mirror to each light source in order to obtain a desired illumination of the object.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
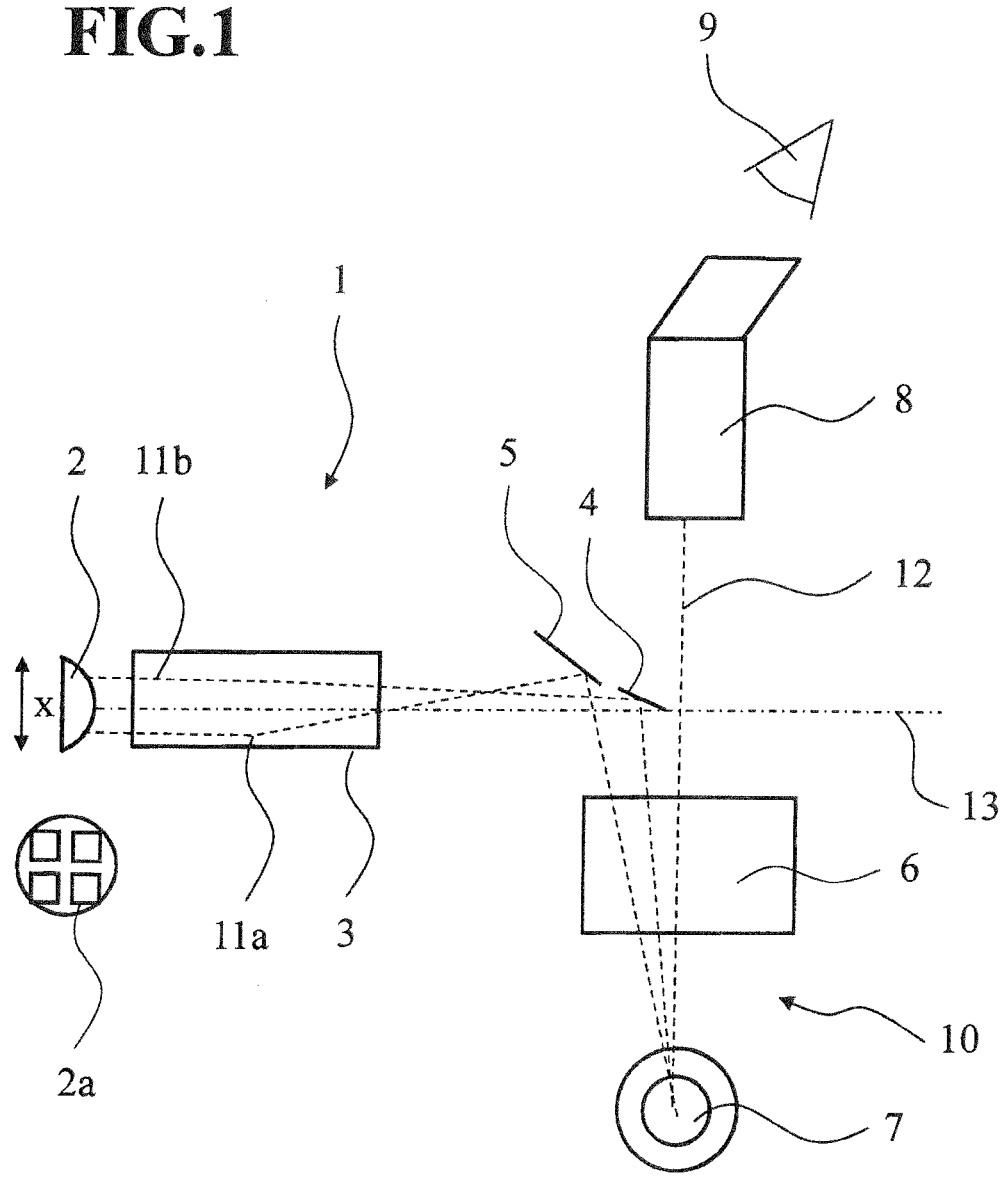
FIG. 1 is a schematic of a surgical microscope having an illumination arrangement according to an embodiment of the invention.

The embodiment depicted in FIG. 1 is a surgical microscope 10 with an illumination arrangement 1 for, for example, undertaking a cataract operation on a patient's eye 7. The illumination arrangement 1 comprises a multichip emitter LED 2 with four light-emitting areas 2a, as indicated by the illustration under the LED 2. Size and shape of the light-emitting areas 2a are, in principle, configurable as desired, for example as a sector of a circle in each case. Illumination optics 3 have an optical axis 13 plotted here by a dash-dotted line, which, for example, may comprise two lenses and one or more stops and which form the light emanating from the LED 2 as desired and, for example, form Köhler optics, serve to guide the light from the multichip emitter LED 2 to the actual surgical microscope 10.

In this case, the illumination pupil is identical to the image of the light source 2. Two mirrors (4, 5) serve here for deflection purposes and, if needed, can also be configured to be semitransparent for guiding the light through further imaging optics 6 to an object field, in particular the eye 7 of a patient to be examined or operated on. Observation optics 8, through which an eye 9 of an observer can see the object field or the eye 7, serve for observation purposes. The basic setup of, for example, the observation optics 8, the imaging optics 6 and further components of a surgical microscope 10 can, for example, be gathered from the aforementioned documents.

As indicated by the two dashed illumination beam paths (11a, 11b) emanating from the LED 2, there is a different illumination of the object field to be examined, or of the eye 7, depending on which light-emitting areas 2a are activated. The illumination beam paths (11a, 11b) are plotted as representing corresponding pencils of light rays. Here, the illumination beam path 11a is obtained by, for example, activating two light-emitting areas 2a above the optical axis 13 and the illumination beam path 11b is obtained by, for example, activating two light-emitting areas 2a below the optical axis 13. Consequently, the light-emitting surface area of the light source is varied perpendicular to the optical axis 13, as indicated by the double-headed arrow (x). It is clear that, alternatively or additionally, a variation of the light-emitting surface area can also be varied in a direction perpendicular to the plane of the drawing. Here, a real illumination beam path 11 passes through the illumination optics 3 along a different optical path than what is only indicated schematically here. Here, different illumination angles for the illumination beam paths (11a, 11b) emanating from different light-emitting areas 2a are not depicted true to scale. Thus, for example, it is possible to implement a 2° or a 6° illumination, that is, at an angle to an observation beam path 12, which is likewise indicated here by a dashed line. Furthermore, the illumination arrangement 1 has no movable components, and so practically no wear-and-tear occurs. Also, it is possible to only generate specifically that illumination beam path (11a, 11b) which is in fact desired. No unwanted light, which subsequently would have to be faded out again or extinguished in a light trap, is generated.

Figure 2:
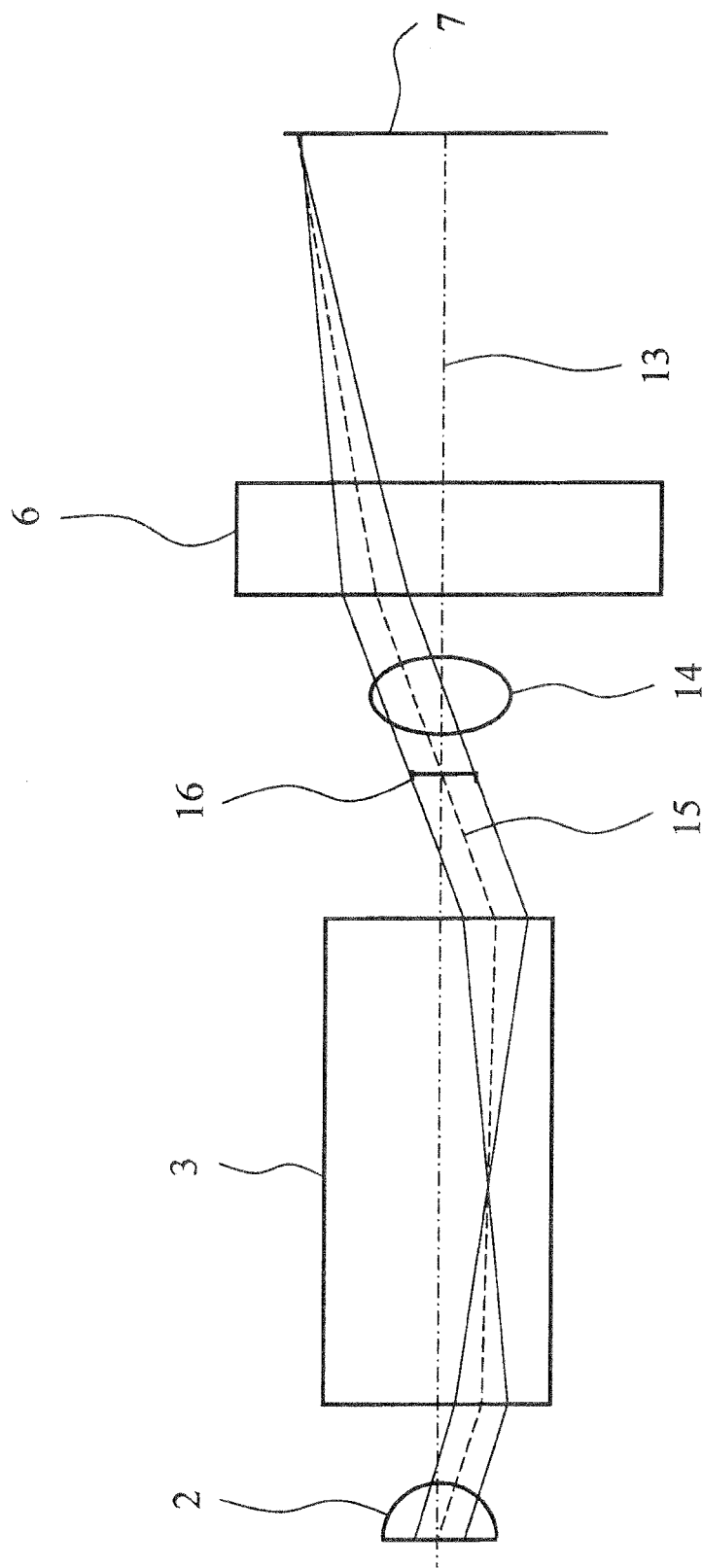
FIG. 2 is a schematic of a Köhler illumination according to a second embodiment of the invention.

FIG. 2 depicts, as an example, the illumination pupil 16 of a Köhler illumination. The light from the light source 2 is focused by the illumination optics 3 and the imaging optics 6 onto the object field or onto the eye 7, wherein the pencil of light rays 14 with the chief ray 15 illuminates the edge of the eye 7. The chief ray 15 intersects the optical axis 13 in the illumination pupil 16. This definition of the illumination pupil 16 applies to all illumination principles, not only the Köhler illumination. In the case of the Köhler illumination, the illumination pupil 16 is identical to the image of the light source 2.

Figure 3:
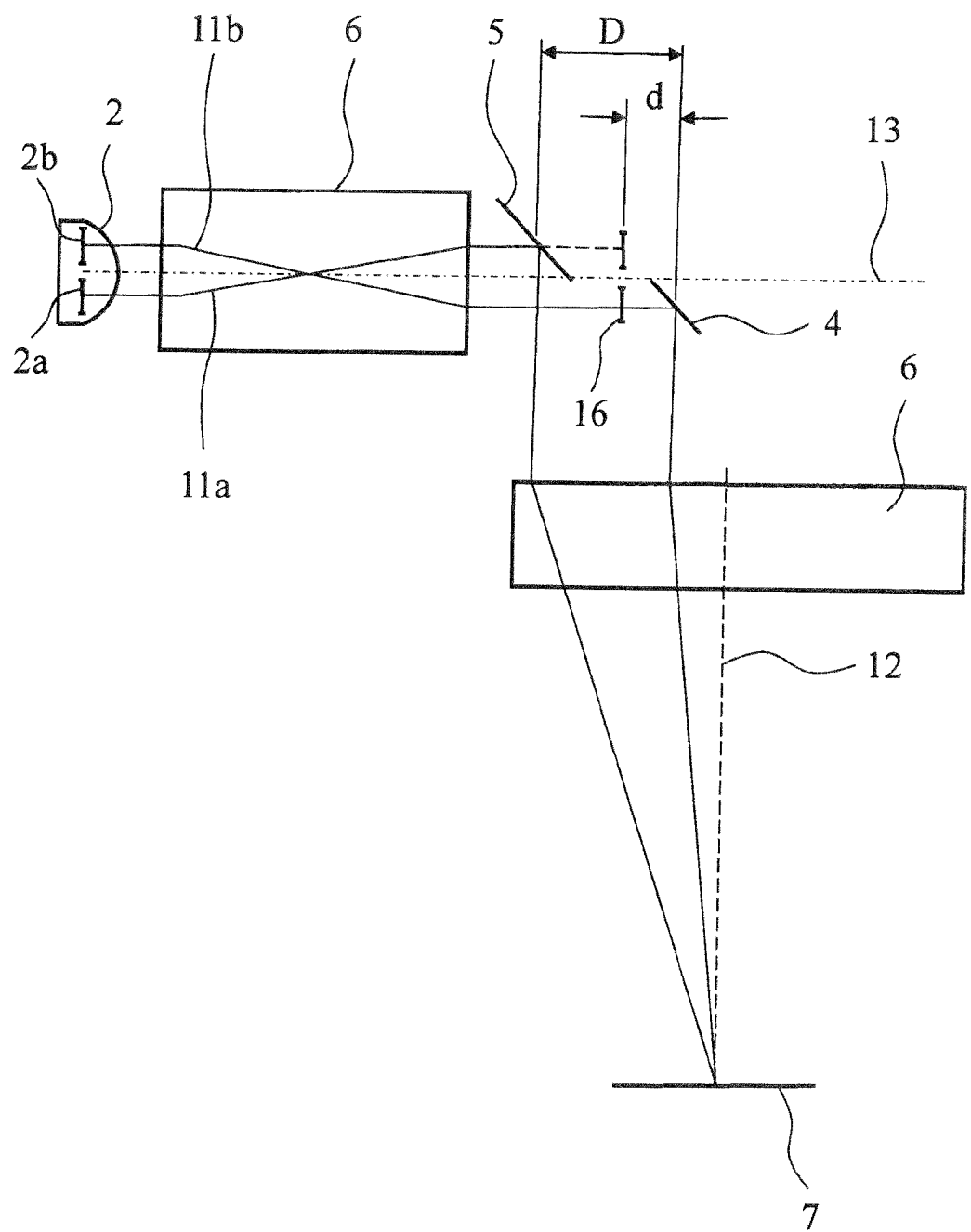
FIG. 3 is a schematic of a Köhler illumination wherein the light source includes two light-emitting areas.

The mirrors 4 and 5 have been omitted for improved clarity; they are preferably arranged upstream or downstream of the illumination pupil, as depicted in FIG. 3.

In FIG. 3, the light source 2 consists of two light-emitting areas (2a, 2b) which are imaged in the illumination pupil 16. Here, the case of the Köhler illumination is once again depicted.

The illumination beam paths 11a and 11b have been plotted as representatives for the pencils of illumination rays and illuminate the object field 7 under different angles. The illumination beam path 11a generates a 6° illumination; the illumination beam path 11b generates a +2° illumination. The observation beam path 12 has also been plotted for clarification purposes.

The illumination pupil 16 lies between the mirrors 4 and 5, with preferably the following applying:

$$d \text{ equals } 0 \text{ to } 0.8 \text{ D},$$

where:
 d=illumination pupil 16–mirror 4 distance
 D=distance between mirror centers
The mirror 4 is the mirror with the smaller area, wherein the mirrors 4 and 5 can also be interchanged. Here, the position of the mirrors (4, 5) should respectively be considered to be the center thereof, as seen along the extent thereof in respect of the optical axis 13.

Figure 4:
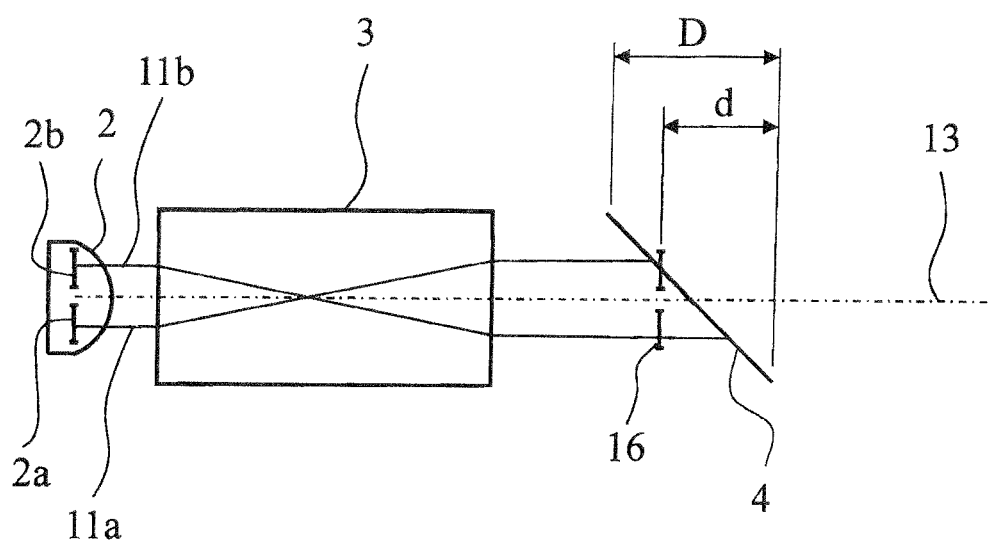
FIG. 4 is a schematic of a Köhler illumination with only a single mirror.

In FIG. 4, the light source 2 consists of two light-emitting areas (2a, 2b) which are imaged in the illumination pupil 16. Here, the case of the Köhler illumination is once again depicted.

The illumination beam paths 11a and 11b have been plotted as representatives for the pencils of illumination rays and illuminate the object field 7 under different angles. The illumination beam path 11b generates a 6° illumination; the illumination beam path 11a generates a +2° illumination. For simplifying the illustration, the imaging optics 6, known per se, and the object field 7 have been omitted.

FIG. 4 depicts the embodiment with only a single mirror 4, with the illumination optics 3 in this case being embodied in such a way that the illumination pupil 16 is imaged within the longitudinal extent of the projection of the mirror 4 on the optical axis 13. In this case, the values are preferably selected as follows:

$$d=0.2 \text{ D to } 0.8 \text{ D},$$

with:
 d=illumination pupil 16–rear mirror edge distance, as seen along the optical axis 13
 D=longitudinal extent of the mirror 4 along the optical axis 13.

Figure 5:
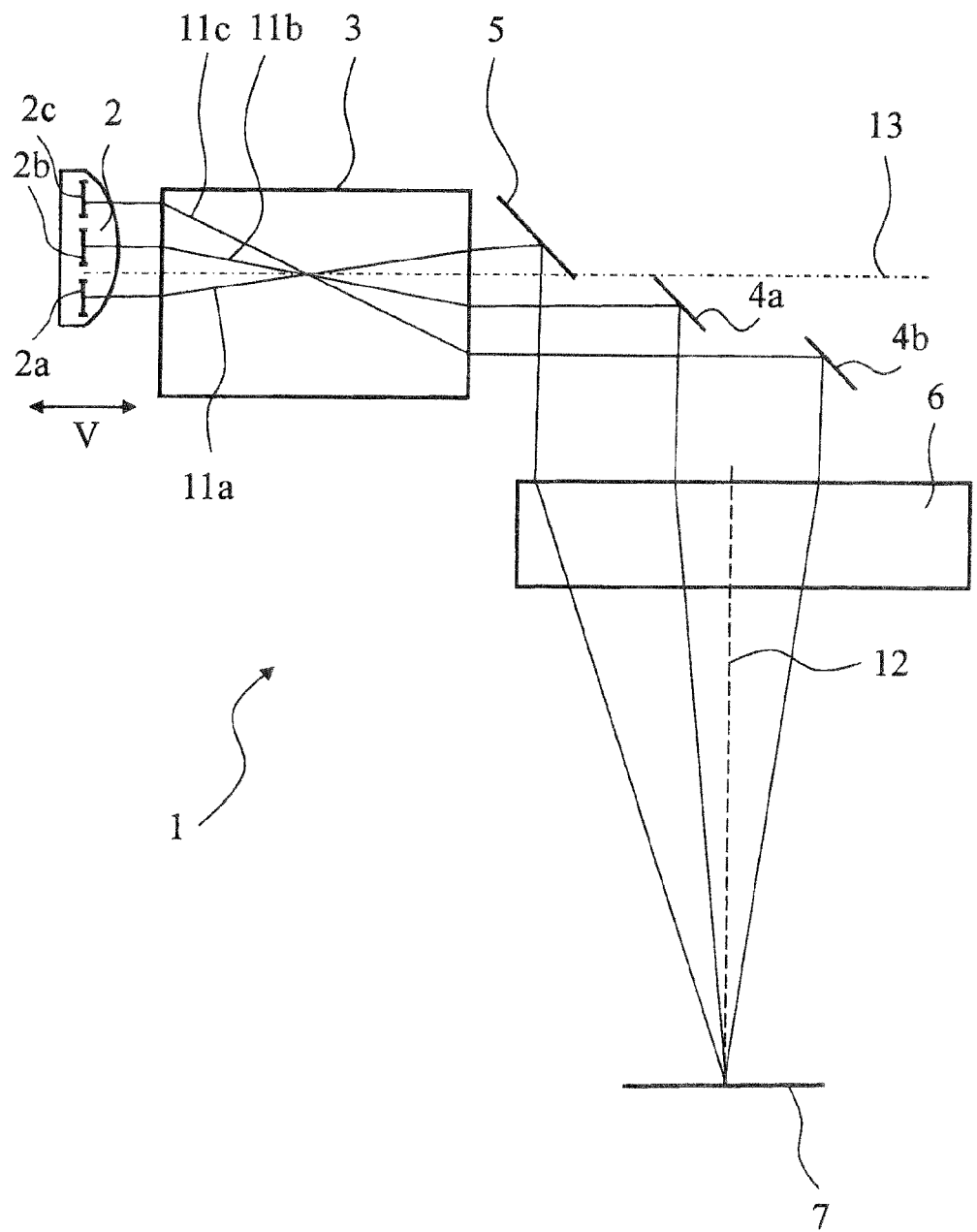
FIG. 5 is a schematic showing an illumination arrangement having a light source with three light-emitting areas; and, FIG. 6 is a schematic of a further illumination arrangement including a light source having three light-emitting areas.

FIG. 5 depicts an illumination arrangement 1 with a light source 2 with three light-emitting areas (2a, b, c), which, as identifiable from the illustration and indicated by the double-headed arrow V, is displaceable, for example by mechanical means, along the optical axis 13. As a result of the embodiment of the illumination optics 3, the illumination beam paths (11a, 11b, 11c) are projected onto the three mirrors (4a, 4b, 5) in such a way that a +/−2° illumination and a 6° illumination can be obtained, depending on which light-emitting area 2a is currently activated. The illumination beam path 11a generates a 6° illumination, the illumination beam path 11b generates a +2° illumination and the illumination beam path 11c generates a −2° illumination. The observation beam path 12 has also been plotted for clarification purposes.

Figure 6:
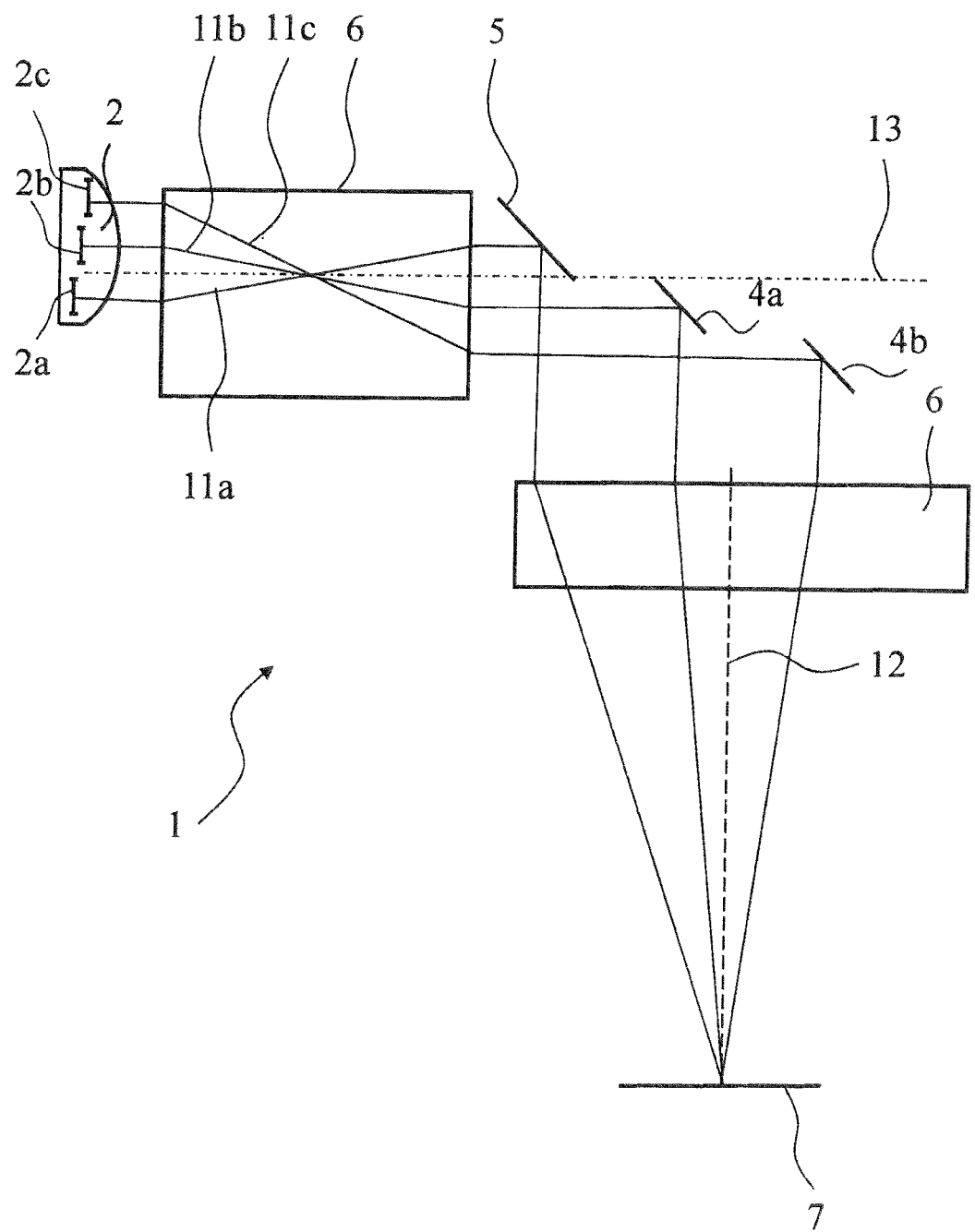

FIG. 6 depicts a further illumination arrangement 1. It comprises a light source 2 with three light-emitting areas (2a, 2b, 2c) which are arranged offset from one another along the optical axis 13. The illumination beam paths (11a, 11b, 11c) emanating from the light-emitting areas (2a, 2b, 2c) are respectively imaged on the mirrors (5, 4a, 4b) by the illumination optics 3. Here, the offset of the light-emitting areas (2a, 2b, 2c) along the optical axis 13 is selected, and the illumination optics 3 are embodied, in such a way that, for example, a 6° illumination can be generated by the illumination beam path 11a and a +2° and −2° illumination can be generated by the illumination beam paths (11b, 11c) when the corresponding light-emitting area (2a, 2b, 2c) is activated.

It is understood that the foregoing description is that of the preferred embodiments of the invention and that various changes and modifications may be made thereto without departing from the spirit and scope of the invention as defined in the appended claims.

LIST OF REFERENCE SIGNS

1 Illumination arrangement
2 Multichip emitter LED
2a Light-emitting area
3 Illumination optics
4 Mirror
5 Mirror
6 Imaging optics
7 Patient's eye
8 Observation optics
9 Observer
10 Surgical microscope
11 Illumination beam path
12 Observation beam path
13 Optical axis of the illumination optics 3
14 Pencil of light rays
15 Chief ray
16 Illumination pupil
x Variation in the position of the light source 2
y Variation in the position of the light source 2 along the optical axis 13
V Displacement of the light source 2 along the optical axis 13

What is claimed is:

1. An illumination arrangement for an optical instrument defining a viewing beam path, the illumination arrangement comprising:
an illumination optic defining an optical axis;
a light source for generating an illumination beam path for illuminating an object field at a specific illumination angle with said viewing beam path;
a mirror arranged in said illumination beam path and being configured to deflect the light of said light source;
said mirror having a longitudinal extent along said optical axis;
said light source having a light-emitting surface region variable perpendicularly to said optical axis without movable parts; and,
said illumination optic being configured to image an illumination pupil within said longitudinal extent of said mirror.

2. The illumination arrangement of claim 1, wherein said light-emitting surface region includes a plurality of light-emitting subregions which can be activated independently from one another.

3. The illumination arrangement of claim 2, wherein said light source is a multichip emitter LED defining said light-emitting subregions.

4. The illumination arrangement of claim 2, wherein said light-emitting subregions have at least one of the following: different colors and different levels of brightness.

5. The illumination arrangement of claim 2, wherein said mirror is a first mirror and wherein said illuminating arrangement comprises a second mirror.

6. The illumination arrangement of claim 5, wherein said illumination arrangement comprises a third mirror.

7. The illumination arrangement of claim 1, wherein said light source is configured to vary said illumination angle to provide different illumination angles.

8. The illumination arrangement of claim 7, wherein said illumination angle lies in a range of 2° to 6°.

9. The illumination arrangement of claim 1, wherein said light source is displaceable along said optical axis.

10. The illumination arrangement of claim 1, wherein said light-emitting surface region defines at least three light-emitting subregions arranged so as to be distributed perpendicular to said optical axis.

11. The illumination arrangement of claim 10, wherein said three light-emitting subregions are offset in two directions.

12. An opththalmologic surgical microscope comprising:
an optical system defining a viewing beam path;
an illumination arrangement including:
an illumination optic defining an optical axis;
a light source for generating an illumination beam path for illuminating an object field at a specific illumination angle with said viewing beam path;
a mirror arranged in said illumination beam path and being configured to deflect the light of said light source;
said mirror having a longitudinal extent along said optical axis;
said light source having a light-emitting surface region variable perpendicularly to said optical axis without movable parts; and,
said illumination optic being configured to image an illumination pupil within said longitudinal extent of said mirror.

* * * * *